United States Patent

Herzig

[11] Patent Number: 6,043,331
[45] Date of Patent: Mar. 28, 2000

[54] ORGANOSILICON COMPOUNDS CONTAINING 1-ALKENYLOXY GROUPS, THEIR PREPARATION AND THEIR USE

[75] Inventor: Christian Herzig, Waging am See, Germany

[73] Assignee: Wacker-Chemie GmbH, Munich, Germany

[21] Appl. No.: 09/119,684

[22] Filed: Jul. 21, 1998

[30] Foreign Application Priority Data

Jul. 24, 1997 [DE] Germany .............. 197 31 961

[51] Int. Cl.⁷ .................................. C08G 77/08
[52] U.S. Cl. ...................... 528/15; 522/99; 528/25; 528/31; 528/33; 556/445
[58] Field of Search ................. 528/15, 25, 31, 528/33; 522/99; 556/445

[56] References Cited

U.S. PATENT DOCUMENTS

| | | |
|---|---|---|
| 4,292,434 | 9/1981 | Lindner et al. |
| 5,057,549 | 10/1991 | Herzig et al. |
| 5,145,915 | 9/1992 | Weitemeyer et al. |
| 5,231,157 | 7/1993 | Herzig et al. |
| 5,250,647 | 10/1993 | Herzig ........................... 528/15 |
| 5,468,890 | 11/1995 | Herzig et al. |
| 5,719,248 | 2/1998 | Herzig et al. ................. 528/15 |

FOREIGN PATENT DOCUMENTS

| | | |
|---|---|---|
| 0105341 | 1/1987 | European Pat. Off. |
| 0110370 | 4/1987 | European Pat. Off. |
| 4215076 | 11/1993 | Germany . |
| 9322368 | 11/1993 | WIPO . |

OTHER PUBLICATIONS

Chemical Abstract CA 107, 1762219.

Primary Examiner—Robert Dawson
Assistant Examiner—Jeffrey B. Robertson
Attorney, Agent, or Firm—Brooks & Kushman P.C.

[57] ABSTRACT

Novel organosilicon compounds containing 1-alkenyloxy groups and comprising units of the formula $$A_a R_b Si x_c O_{\frac{4-(a+b+c)}{2}}, \quad (I)$$

where R are identical or different and are each a monovalent, halogenated or unhalogenated hydrocarbon radical having from 1 to 18 carbon atom(s) per radical, X are identical or different and are each a chlorine atom or a radical of the formula $-OR^1$, where $R^1$ is an alkyl radical having from 1 to 8 carbon atom(s) per radical which may be substituted by an ether oxygen atom, a is 0 or 1, b is 0, 1, 2 or 3, c is 0, 1, 2 or 3, and the sum $a+b+c \leq 4$, A is a radical of the formula $$\begin{array}{c} HC[R^4(OR^3)_zOCH{=}CR^2]_xH \\ \parallel \\ {-}C[R^4(OR^3)_zOCH{=}CR^2]_yH \end{array}$$

where x is 0 or 1 and y is 0 or 1, with the proviso that the sum $x+y$ is 1 or 2, z is 0 or an integer from 1 to 12, $R^2$ is a hydrogen atom or a methyl radical, $R^3$ can be identical or different and are each a linear or branched alkylene radical having from 1 to 6 carbon atom(s) per radical, $R^4$ is a linear or branched alkylene radical having from 1 to 6 carbon atom(s) per radical, with the proviso that at least one radical A is present per molecule, are described.

10 Claims, No Drawings

ORGANOSILICON COMPOUNDS CONTAINING 1-ALKENYLOXY GROUPS, THEIR PREPARATION AND THEIR USE

TECHNICAL FIELD

The invention relates to organosilicon compounds containing 1-alkenyloxy groups and also to a process for their preparation. Furthermore, the invention relates to compositions which are based on organosilicon compounds containing 1-alkenyloxy groups which can be crosslinked by means of light.

BACKGROUND ART

EP-B 105 341 (General Electric Company; published on Jan. 7, 1987) discloses organopolysiloxanes which contain, per molecule, at least one Si-bonded vinyloxy functional group of the formula $$H_2C=CH-O-G-$$

where G is an alkylene radical or an alkylene radical which is interrupted by at least one divalent heteroradical such as —O—, a divalent phenylene radical or substituted divalent phenylene radical, or a combination of such radicals. These organopolysiloxanes are obtained by preparation of a compound containing one allyl and one vinyloxy group and addition of this compound onto the SiH groups of the polyorganosiloxanes, with the hydrosilylation occurring only on the allyl group. EP-B 105 341 also describes compositions which can be crosslinked by means of light and comprise the abovementioned organopolysiloxanes, and also onium salts which catalyze the cationic polymerization of these organopolysiloxanes.

Chemical Abstracts 107,176221q discloses the production of plastic lenses using a silane containing a vinyloxypropyl group and at least one trimethylsiloxy group, which silane is obtained by hydrosilylation of allyl vinyl ether with a trimethylsiloxy-containing silane, with the addition occurring on the allyl group.

US-A 5,057,549 (Wacker-Chemie GmbH; issued on Oct. 15, 1991) and US-A 5,231,157 (Wacker-Chemie GmbH; issued on Jul. 27, 1993) describe propenyloxy-containing organopolysiloxanes or propenyloxy-containing siloxane copolymers which are prepared in a two-stage process by addition of compounds containing two or more allyloxy groups onto SiH groups of organopolysiloxanes and subsequent conversion of the allyloxy groups into the propenyloxy groups by rearrangement of the double bond.

US-A 5,145,915 (Goldschmidt AG; issued on Sep. 8, 1992) discloses organopolysiloxanes containing any number of substituted vinyl ether groups which are prepared by hydrosilylation, i.e. by reaction of an organopolysiloxane containing SiH groups with a polyoxyalkylene ether, for example of the formula

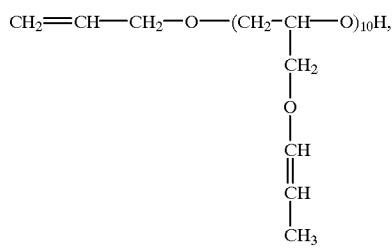

with the addition occurring on the allyl group.

DE-A 42 15 076 (Wacker-Chemie GmbH; published on November 11, 1993) describes vinyloxy-containing siloxane copolymers which are prepared by reaction of organic compounds containing a plurality of vinyloxy groups with organopolysiloxanes containing Si-bonded hydrogen atoms in the presence of hydrosilylation catalysts. Since the vinyloxy groups are all equally reactive, the hydrosilylation reaction does not occur selectively and the vinyloxy-containing organic compound has to be used in large excesses in order to obtain the desired vinyl ether siloxanes.

SUMMARY OF THE INVENTION

It is an object of the invention to provide organosilicon compounds containing 1-alkenyloxy groups which can be prepared with high selectivity in a simple process which allows more than one 1-alkenyloxy group to be introduced on one silicon atom. Another object of the invention is to provide organosilicon compounds which contain 1-alkenyloxy groups and undergo crosslinking by cationic polymerization particularly rapidly under the action of light, in particular ultraviolet light. These objects are achieved by the invention.

DETAILED DESCRIPTION OF THE INVENTION

The invention provides organosilicon compounds which contain 1-alkenyloxy groups and comprise units of the formula $$A_aR_bSiX_cO_{\frac{4-(a+b+c)}{2}} \tag{I}$$

where R are identical or different and are each a monovalent, halogenated or unhalogenated hydrocarbon radical having from 1 to 18 carbon atom(s) per radical, X are identical or different and are each a chlorine atom or a radical of the formula $-OR^1$, where $R^1$ is an alkyl radical having from 1 to 8 carbon atom(s) per radical which may be substituted by an ether oxygen atom, a is 0 or 1, b is 0, 1, 2 or 3, c is 0, 1, 2 or 3, and the sum $a+b+c \leq 4$ and A is a radical of the formula

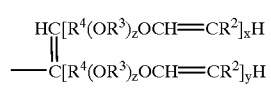

where x is 0 or 1 and y is 0 or 1, with the proviso that the sum x+y is 1 or 2, z is 0 or an integer from 1 to 12, $R^2$ is a hydrogen atom or a methyl radical, each $R^3$ is identical or different and is a linear or branched alkylene radical having from 1 to 6 carbon atom(s) per radical, $R^4$ is a linear or branched alkylene radical having from 1 to 6 carbon atom(s) per radical, with the proviso that at least one radical A is present per molecule.

The invention further provides a process for preparing the organosilicon compounds containing 1-alkenyloxy groups, which comprises adding an organic compound (1) of the formula

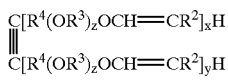

where $R^2$, $R^3$, $R^4$, x, y and z are as defined above, onto an organosilicon compound (2) containing at least one Si-bonded hydrogen atom per molecule in the presence of a catalyst (3) which promotes the addition of Si-bonded hydrogen onto aliphatic multiple bonds.

The organosilicon compounds of the invention are preferably silanes or organopolysiloxanes.

The organosilicon compounds of the invention preferably have an average molecular weight ($M_n$) of from 200 to 1,000,000 g/mol, preferably from 300 to 50,000 g/mol, and preferably have a viscosity of from 5 to 1,000,000 $mm^2 \cdot s^{-1}$ at 25° C., preferably from 20 to 100,000 $mm^2 \cdot s^{-1}$ at 25° C.

Examples of radicals R are alkyl radicals such as the methyl, ethyl, n-propyl, iso-propyl, 1-n-butyl, 2-n-butyl, iso-butyl, tert-butyl, n-pentyl, iso-pentyl, neo-pentyl and tert-pentyl radicals; hexyl radicals such as the n-hexyl radical; heptyl radicals such as the n-heptyl radical; octyl radicals such as the n-octyl radical and iso-octyl radicals such as the 2,2,4-trimethylpentyl radical; nonyl radicals such as the n-nonyl radical; decyl radicals such as the n-decyl radical; dodecyl radicals such as the n-dodecyl radical; octadecyl radicals such as the n-octadecyl radical; cycloalkyl radicals such as cyclopentyl, cyclohexyl, cycloheptyl and methylcyclohexyl radicals; aryl radicals such as the phenyl, naphthyl, anthryl and phenanthryl radicals; alkaryl radicals such as o-, m-, p-tolyl radicals, xylyl radicals and ethylphenyl radicals; and aralkyl radicals such as the benzyl radical, the α- and β-phenylethyl radicals. Preference is given to the methyl radical.

Examples of halogenated radicals R are haloalkyl radicals such as the 3,3,3-trifluoro-n-propyl radical, the 2,2,2,2',2',2'-hexafluoroisopropyl radical, the heptafluoroisopropyl radical and haloaryl radicals such as the o-, m-, and p-chlorophenyl radicals.

Examples of alkyl radicals $R^1$ are methyl, ethyl, n-propyl, iso-propyl, 1-n-butyl, 2-n-butyl, iso-butyl and tert-butyl radicals. Preference is given to the methyl and ethyl radicals. Examples of alkyl radicals $R^1$ which are substituted by an ether oxygen atom are the methoxyethyl and ethoxyethyl radicals.

The radical $R^2$ is preferably a hydrogen atom.

$R^3$ is preferably a radical of the formula $-CH_2CH_2-$,

or $-CH_2CH_2CH_2CH_2-$.

Examples of alkylene radicals $R^4$ are those of the formulae $-(CH_2)-$, $-CH(CH_3)-$, $-C(CH_3)_2-$, $-C(CH_3)(C_2H_5)-$, $-(CH_2)_2-$, and $-(CH_2)_4-$; preference is given to the radical of the formula $-(CH_2)-$.

Preferably, a is on average from 0.01 to 1.0, b is on average from 0.0 to 3.0, c is on average from 0.0 to 3.0 and the sum a+b+c is on average from 1.5 to 4.0.

Examples of radicals A are those of the formula

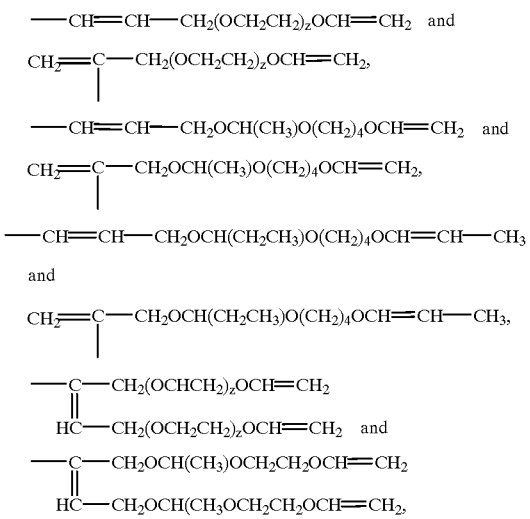

where z is as defined above, and is preferably from 1 to 5, particularly preferably from 1 to 3.

Preferred silanes containing 1-alkenyloxy groups are those of the formula $$AR_dSiX_{3-d} \qquad (II)$$

where A, R and X are as defined above and d is 0, 1 or 2.

Preferred organopolysiloxanes containing 1-alkenyloxy groups are those of the formula $$A_gR_{3-g}SiO(SiR_2O)_n(SiRAO)_mSiR_{3-g}A_g \qquad (III)$$

where A and R are as defined above, g is 0 or 1, n is 0 or an integer from 1 to 1500 and m is 0 or an integer from 1 to 100, with the proviso that at least one radical A is present per molecule.

Examples of organic compounds (1) which are used in the process of the invention are those of the formulae $HC\equiv C-CH_2(OCH_2CH_2)_zOCH=CH_2$ $HC\equiv C-CH_2OCH(CH_3)O(CH_2)_4OCH=CH_2$ $HC\equiv C-CH_2OCH(CH_2CH_3)O(CH_2)_4OCH=CH-CH_3$

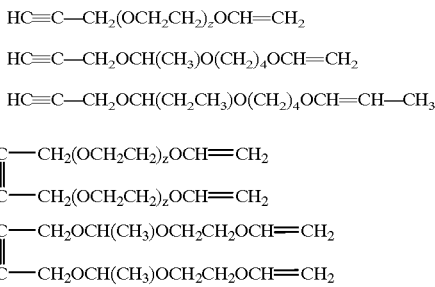

where z is as defined above, and is preferably from 1 to 5, particularly preferably from 1 to 3.

The organic compounds (1) are prepared by vinylating the parent (alkoxylated) alkynols or alkynediols by generally known methods of Reppe chemistry using alkynes, preferably using acetylene, thus introducing the $-CH=CR^2H$ group. Alternatively, if some or all of the radials $R^3$ are 1,1-substituted hydrocarbon radicals, the compound (1) can also be prepared by acid-catalyzed addition of divinyl ethers onto alkynols or alkynediols. The compounds (1) can be very easily obtained in this way. These products are advantageously purified by distillation.

As organosilicon compounds (2) containing at least one Si-bonded hydrogen atom per molecule, preference is given to using silanes containing one Si-bonded hydrogen atom per molecule or organopolysiloxanes containing at least one Si-bonded hydrogen atom per molecule and having the formula $$H_eR_fSiO_{\frac{4-(e+f)}{2}}$$  (IV)

where R is as defined above, e is 0 or 1, f is 0, 1, 2 or 3 and the sum e+f is not greater than 3.

Preferably, e is on average from 0.01 to 1.0 and f is on average from 0.0 to 3.0.

The organopolysiloxanes (2) containing at least one Si-bonded hydrogen atom per molecule preferably contain at least 0.04% by weight, preferably from 0.1 to 1.6% by weight, of Si-bonded hydrogen and their average viscosity is preferably from 2 to 20,000 $mm^2 \cdot s^{-1}$ at 25° C., preferably from 2 to 2000 $mm^2 \cdot s^{-1}$ at 25° C., particularly preferably from 2 to 200 $mm^2 \cdot s^{-1}$ at 25° C.

As silanes containing one Si-bonded hydrogen atom per molecule, preference is given to using those of the formula $$HR_dSi(OR^1)_{3-d}$$  (V)

where R, $R^1$ and d are as defined above.

As organopolysiloxanes containing at least one Si-bonded hydrogen atom per molecule, preference is given to using those of the formula $$H_hR_{3-h}SiO(SiR_2O)_O(SiRHO)_pSiR_{3-h}H_h$$  (VI)

where R is as defined above, h is 0 or 1, o is 0 or an integer from 1 to 1500 and p is 0 or an integer from 1 to 100.

A preferred example of silanes of the formula (V) is triethoxysilane. Preferred examples of organopolysiloxanes of the formula (VI) are copolymers of dimethylhydrogensiloxane and dimethylsiloxane units, copolymers of dimethylhydrogensiloxane, dimethylsiloxane and methylhydrogensiloxane units, copolymers of trimethylsiloxane and methylhydrogensiloxane units, and copolymers of trimethylsiloxane, dimethylsiloxane and methylhydrogensiloxane units.

Methods of preparing organopolysiloxanes containing at least one Si-bonded hydrogen atom per molecule, including those of the preferred type, are generally known.

In the process of the invention, the organic compound (1) is preferably used in such amounts that from 1 to 2 mol, preferably from 1.05 to 1.20 mol, of organic compound (1) is present per gram atom of Si-bonded hydrogen in the organosilicon compound (2).

In some cases, if the organosilicon compound (2) containing Si-bonded hydrogen atoms can be removed by distillation more easily than the organic compound (1), the organic compound (1) can be used in amounts of less than 1 mol, but in an amount of at least 0.8 mol, per gram atom of Si-bonded hydrogen in the organosilicon compound (2).

In the process of the invention, as catalysts (3) which promote the addition of Si-bonded hydrogen onto aliphatic multiple bonds, it is possible to use the same catalysts as have also been able to be used hitherto to promote the addition of Si-bonded hydrogen onto aliphatic multiple bonds. The catalysts (3) are preferably metals selected from the platinum metal group or compounds or complexes of platinum group metals. Examples of such catalysts are metallic and finely-divided platinum which can be present on supports such as silicon dioxide, aluminum oxide or activated carbon, compounds or complexes of platinum such as platinum halides, e.g. $PtCl_4$, $H_2PtCl_6 \cdot 6H_2O$, $Na_2PtCl_4 \cdot 4H_2O$, platinum-olefin complexes, platinum-alcohol complexes, platinum alkoxide complexes, platinum-ether complexes, platinum-aldehyde complexes, platinum-ketone complexes including reaction products of $H_2PtCl_6 \cdot 6H_2O$ and cyclohexanone, platinum-vinylsiloxane complexes such as platinum-1,3-divinyl-1,1,3,3-tetramethyldisiloxane complexes with or without a content of detectable, inorganically bound halogen, bis(gamma-picoline)platinum dichloride, trimethylenedipyridineplatinum dichloride, dicyclopentadieneplatinum dichloride, (dimethyl sulfoxide) (ethylene)platinum(II) dichloride, cyclooctadieneplatinum dichloride, norbornadieneplatinum dichloride, gamma-picolineplatinum dichloride, cyclopentadieneplatinum dichloride and also reaction products of platinum tetrachloride with olefin and primary amines or secondary amines or primary and secondary amines as described in US-A 4,292,434, e.g. the reaction product of platinum tetrachloride dissolved in 1-octene with sec-butylamine, or ammonium-platinum complexes as described in EP-B 110 370.

The catalyst (3) is preferably used in amounts of from 2 to 200 ppm by weight (parts by weight per million parts by weight), preferably in amounts of from 5 to 50 ppm by weight, in each case calculated as elemental platinum and based on the total weight of organic compound (1) and organosilicon compound (2).

The process of the invention is preferably carried out at the pressure of the surrounding atmosphere, i.e. at about 1020 hPa (abs.), but it can also be carried out at higher or lower pressures. Furthermore, the process of the invention is preferably carried out at a temperature of from 80° C. to 150° C., preferably from 110° C. to 125° C.

In the process of the invention, it is possible to make concomitant use of inert, organic solvents, although the concomitant use of inert, organic solvents is not preferred. Examples of inert, organic solvents are toluene, xylene, octane isomers and butyl acetate.

Excess organic compounds (1) and any inert organic solvent used are preferably removed by distillation from the alkenyl-containing organosilicon compounds prepared by the process of the invention.

The process of the invention can be carried out batchwise, semicontinuously or fully continuously.

The novel organosilicon compounds containing vinyloxy groups are cationically crosslinkable, for example by addition of acids such as hydrochloric acid, sulfuric acid or p-toluenesulfonic acid. The novel siloxane copolymers containing vinyloxy groups are preferably crosslinked in a cationic polymerization initiated by light. As catalysts for the light-initiated crosslinking, preference is given to using onium salts selected from the group having the formulae $$R'_2I^+X^-, R'_3S^+X^-, R'_3Se^+X^-, R'_4P^+X^- \text{ and } R'_4N^+X^-,$$

where R' can be identical or different and are each a monovalent organic radical having from 1 to 30 carbon atoms and X⁻ is a tosylate anion or a weakly nucleophilic or non-nucleophilic anion Y⁻ selected from the group consisting of $CF_3CO_2^-$, $BF_4^-$, $PF_6^-$, $AsF_6^-$, $SbF_6^-$, $ClO_4^-$, $HSO_4^-$, $CF_3SO_3^-$ and $C_4F_9SO_3$, which are known from EP-B 105 341 as cited at the outset and US-A 5,468,890 (Wacker-Chemie GmbH; issued on Nov. 21, 1995).

Examples of radicals R' are hydrocarbon radicals including aromatic carbocyclic radicals having from 6 to 20 carbon atoms which may be substituted by from 1 to 4 monovalent radicals selected from the group consisting of $C_{1-8}$-alkoxy, $C_{1-8}$-alkyl, nitro, chloro, bromo, cyano, carboxy and mercapto radicals and including aromatic heterocyclic radicals such as the pyridyl, thiophenyl and pyranyl radicals.

Examples of such onium salts are diaryliodonium salts and triarylsulfonium salts, for example the bis(dodecylphenyl)iodonium salts described in EP-B 105 341, e.g. bis(dodecylphenyl)iodonium hexa-fluoroantimonate or bis(dodecylphenyl)iodonium hexa-fluoroarsenate, or iodonium salts described in US-A 5,468,890 and having the formula

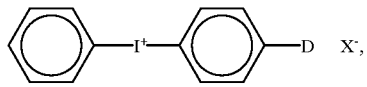

where D is a radical of the formula

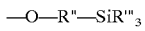

where

R" is a divalent hydrocarbon radical having from 1 to 18 carbon atoms per radical which may be interrupted by at least one oxygen atom and/or sulfur atom and/or carboxyl group, R'" is a monovalent hydrocarbon radical having from 1 to 18 carbon atoms per radical which may be interrupted by at least one oxygen atom, and X⁻ is as defined above.

The invention accordingly provides for the use of the novel organosilicon compounds containing 1-alkenyloxy groups in compositions which are based on the abovementioned organosilicon compounds and can be crosslinked by means of light.

The novel organosilicon compounds containing 1-alkenyloxy groups are preferably crosslinked by means of ultraviolet light, preferably ultraviolet light having wavelengths in the range from 200 to 400 nm. The ultraviolet light can be generated, for example, in xenon, mercury low-pressure, mercury medium-pressure, or mercury high-pressure lamps. Light having a wavelength of from 400 to 600 nm, i.e. "halogen light", is also suitable for crosslinking by means of light. The novel organosilicon compounds containing 1-alkenyloxy groups can be crosslinked by light in the visible region if concomitant use is made of commercial photosensitizers.

The cationic polymerization of the novel siloxane copolymers containing vinyloxy groups can naturally also be initiated by Bronsted or Lewis acids customary for this purpose.

Finally, the invention also provides for the use of the novel organosilicon compounds containing 1-alkenyloxy groups for producing coatings which can be crosslinked by means of light, for example for producing coatings of release paper.

The novel siloxane copolymers containing vinyloxy groups can also be used in radiation-curing printing inks.

Examples of surfaces to which the coatings according to the invention can be applied are those of paper, wood, cork, plastic films, e.g. polyethylene films or polypropylene films, ceramic articles, glass including glass fibers, metals, board including that made of asbestos and of woven and nonwoven fabric made of natural or synthetic organic fibers.

The application of the novel siloxane copolymers containing vinyloxy groups to the surfaces to be coated can be carried out in any manner which is suitable and generally known for the production of coatings from liquid materials, for example by dipping, painting, casting, spraying, rolling on, printing, e.g. by means of an offset gravure coating apparatus, or by knife or blade coating.

EXAMPLE 1

12 g of acetaldehyde propynyl 4-vinyloxybutyl acetal of the formula $HC≡CCH_2OCH(CH_3)O(CH_2)_4OCH=CH_2$, prepared by addition of propargyl alcohol onto butanediol divinyl ether in the presence of 50 ppm of p-toluenesulfonic acid as catalyst and subsequent purification by distillation, are treated with 5.5 mg of platinum-1,3-divinyl-1,1,3,3-tetramethyldisiloxane complex (about 1.5 mg of Pt) and heated to 115° C. 25 g of an α,ω-dihydrogendimethylpolysiloxane containing 0.20% by weight of Si-bonded hydrogen are metered into this mixture, with the temperature rising to 120° C. The product has a viscosity of 23 mm²/s at 25° C. and an average of 14 siloxane units per molecule. The ¹H-NMR spectrum indicates hydrosilylation exclusively at the acetylenic triple bond with signals at 5.5 and 5.8 ppm for the 2-dimethylsiloxy product (54%) and 5.9 and 6.15 ppm for the 3-dimethylsiloxy product (46%). A signal at 0.9 ppm for an $SiCH_2(CH_2O)$ configuration which may have been formed by hydrosilylation at the vinyl ether group cannot be seen in the spectrum. The vinyl ether siloxane contains about 1.7 mol of vinyl ether groups per kg.

EXAMPLE 2

The procedure of Example 1 is repeated, except that the acetal of Example 1 is replaced by 15 g of an acetal of the formula

prepared from ethoxylated propargyl alcohol and butanediol divinyl ether by the method mentioned in Example 1. This gives a vinyl ether siloxane polymer having a viscosity of 26 mm²/s at 25° C. and an average chain length of 14 siloxane units per molecule. The ¹H-NMR spectrum shows only signals for hydrosilylation at the triple bond. The ratio of 2-dimethylsiloxy to 3-dimethylsiloxy is 53:47. The vinyl ether double bond was not hydrosilylated. The product contains 1.6 mol of vinyl ether groups per kg.

EXAMPLE 3

The procedure of EXAMPLE 1 is repeated, except that the α,ω-dihydrogendimethylpolysiloxane is replaced by 36 g of an equilibrate comprising hydrogendimethylsiloxane, hydrogenmethylsiloxane and dimethylsiloxane units and having a viscosity of 29 mm²/s at 25° C. and containing 0.14% by weight of Si-bonded hydrogen. This gives a product having a viscosity of 70 mm²/s at 25° C.

Even when using hydrogenmethylsiloxane units, the ¹H-NMR spectrum indicates no hydrosilylation at the vinyl ether group. The hydrosilylation of the alkyne ether group is evidenced by a series of signals from 5.5 to 6.3 ppm. The polymer contains about one mol of vinyl ether groups per kg.

EXAMPLE 4

The procedure of Example 1 is repeated, except that the monoacetal of Example 1 is replaced by 20.4 g of a reaction product of 2-butyne-1,4-diol with an excess of ethylene glycol divinyl ether, which consists of the diacetal of the formula $$H_2C=CHOCH_2CH_2OCH(CH_3)OCH_2C\equiv CCH_2OCH(CH_3)$$
$$OCH_2CH_2OCH=CH_2$$

and the tetraacetal of the formula $$H_2C=CHOCH_2CH_2OCH(CH_3)OCH_2C\equiv CCH_2OCH(CH_3)$$
$$OCH_2CH_2—$$
$$OCH_2CH_2OCH(CH_3)OCH_2C\equiv CCH_2OCH(CH_3)OCH_2C$$
$$H_2OCH=CH_2.$$

After the dropwise addition, the mixture is allowed to react further for 1 hour. This gives a polymer product having a viscosity of 163 mm$^2$/s at 25° C. and containing about 2.2 mol of vinyloxy groups per kg. The $^1$H-NMR spectrum again indicates that hydrosilylation occurs exclusively at the C≡C triple bond (multiplet at 6.0 ppm), while the signal for an SiCH$_2$(CH$_2$O) group which may be formed by reaction at the vinyl ether group is absent.

EXAMPLE 5

200 mg of a 50% strength solution of tris[3-(3-dimethyloctylsilylpropyl)-4-butoxyphenyl]sulfonium hexafluoroantimonate in isopropyl myristate are homogeneously mixed into 10.0 g of the vinyl ether-containing siloxane polymer prepared in EXAMPLE 2 and the mixture is applied in a layer about 4 μm thick to HDPE film by doctor blade coating.

Illumination with a mercury intermediate-pressure lamp (80 W/cm) at a distance of about 10 cm gave, after about 0.2 seconds, an abrasion-resistant, cured coating.

This generation of the heat of polymerization of the same ready-to-use mixture is measured in a photo-DSC apparatus (DPA 7 from Perkin-Elmer). Broad band irradiation at a power density of 170 mW/cm$^2$ gives a total energy output of 98 joule/g.

What is claimed is:

1. An organosilicon compound containing 1-alkenyloxy groups and comprising units of the formula

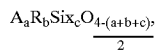
(I)

where each R is identical or different and is a monovalent, halogenated or unhalogenated hydrocarbon radical having from 1 to 18 carbon atom(s) per radical, each X is identical or different and is a chlorine atom or a radical of the formula —OR$^1$, where R$^1$ is an alkyl radical having from 1 to 8 carbon atom(s) per radical which may be substituted by an ether oxygen atom, a is 0 or 1, b is 0, 1, 2 or 3, c is 0, 1, 2 or 3, and the sum a+b+c≦4, A is a radical of the formula

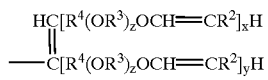

where x is 0 or 1 and y is 0 or 1, with the proviso that the sum x+y is 1 or 2, z is 0 or an integer from 1 to 12, R$^2$ is a hydrogen atom or a methyl radical, each R$^3$ is identical or different and is a linear or branched alkylene radical having from 1 to 6 carbon atom(s) per radical, R$^4$ is a linear or branched alkylene radical having from 1 to 6 carbon atom(s) per radical, with the proviso that at least one radical A is present per molecule.

2. A photocrosslinkable composition comprising one or more of the organosilicon compounds containing 1-alkenyloxy groups of claim 1.

3. A cationically crosslinkable composition comprising one or more of the organosilicon compounds containing 1-alkenyloxy groups of claim 1.

4. A crosslinked coating comprising the photochemically crosslinked composition of claim 2.

5. A crosslinked coating comprising the cationically crosslinked composition of claim 3.

6. A process for preparing an organosilicon compound containing 1-alkenyloxy groups, which comprises adding an organic compound (1) of the formula

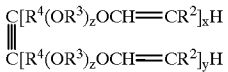

where R$^2$, R$^3$, R$^4$, x, y and z are as defined in claim 1, onto an organosilicon compound (2) containing at least one Si-bonded hydrogen atom per molecule in the presence of a catalyst (3) which promotes the addition of Si-bonded hydrogen onto aliphatic multiple bonds.

7. A process for the preparation of a crosslinked organosilicon composition, said process comprising crosslinking a crosslinkable composition prepared by the process of claim 6.

8. The process of claim 7 wherein said step of crosslinking comprises crosslinking in the presence of an effective amount of a cationic crosslinking catalyst.

9. The process of claim 7, wherein said step of crosslinking comprises photochemical crosslinking.

10. The process of claim 9 wherein said photochemical crosslinking takes place in the presence of an effective amount of a cationic photochemical crosslinking catalyst.

* * * * *